(12) United States Patent
Cook et al.

(10) Patent No.: US 8,188,184 B2
(45) Date of Patent: May 29, 2012

(54) ADDITIVE AND VEHICLE FOR INKS, PAINTS, COATINGS AND ADHESIVES

(75) Inventors: Leroy John Cook, Lake Bluff, IL (US); Richard T. Skov, Spencer, MA (US)

(73) Assignee: Omnitech Environmental, LLC, Lake Bluff, IL (US)

( * ) Notice: Subject to any disclaimer, the term of this patent is extended or adjusted under 35 U.S.C. 154(b) by 0 days.

(21) Appl. No.: 12/956,362

(22) Filed: Nov. 30, 2010

(65) Prior Publication Data
US 2011/0086957 A1   Apr. 14, 2011

Related U.S. Application Data

(62) Division of application No. 11/009,577, filed on Dec. 10, 2004, now Pat. No. 7,863,485.

(51) Int. Cl.
| | |
|---|---|
| *C08F 8/00* | (2006.01) |
| *C08F 8/30* | (2006.01) |
| *C08F 26/04* | (2006.01) |
| *C08F 283/04* | (2006.01) |
| *C08F 290/14* | (2006.01) |
| *C08G 18/08* | (2006.01) |
| *C08G 63/48* | (2006.01) |
| *C08G 63/91* | (2006.01) |
| *C08J 3/00* | (2006.01) |
| *C08K 3/20* | (2006.01) |
| *C08L 29/04* | (2006.01) |
| *C08L 75/00* | (2006.01) |
| *C09D 5/00* | (2006.01) |
| *C09D 11/00* | (2006.01) |

(52) U.S. Cl. ......... 525/50; 523/160; 523/161; 524/507; 524/591; 524/839; 524/840; 525/55; 525/57; 525/59; 525/61; 525/123; 525/455

(58) Field of Classification Search .................. 523/160, 523/161; 525/50, 55, 57, 59, 61, 123, 455; 524/507, 591, 839, 840
See application file for complete search history.

(56) References Cited

U.S. PATENT DOCUMENTS

| | | | |
|---|---|---|---|
| 3,926,641 A | 12/1975 | Rosen | |
| 4,100,047 A | 7/1978 | McCarty | |
| 4,102,827 A | 7/1978 | Rembaum et al. | |
| 4,105,518 A | 8/1978 | McGinniss | |
| 4,148,987 A | 4/1979 | Winey | |
| 4,301,186 A | 11/1981 | Mayer et al. | |
| 4,374,670 A | 2/1983 | Slocombe | |
| 4,898,656 A | 2/1990 | Hoshino et al. | |
| 4,948,819 A | 8/1990 | Green et al. | |
| 5,128,386 A | 7/1992 | Rehmer et al. | |
| 5,235,015 A | 8/1993 | Ali et al. | |
| 5,248,805 A | 9/1993 | Boettcher et al. | |
| 5,501,942 A | 3/1996 | Salvin et al. | |

FOREIGN PATENT DOCUMENTS

| | | |
|---|---|---|
| JP | 50071794 | 6/1975 |
| WO | WO 2004/044067 A1 | 5/2004 |

OTHER PUBLICATIONS

U.S. Appl. No. 08/511,020, filed Aug. 3, 1995, Cook et al.
U.S. Appl. No. 08/511,021, filed Aug. 3, 1995, Cook et al.
U.S. Appl. No. 09/637,052, filed Aug. 11, 2000, Cook et al.
International Search Report for corresponding PCT Application No. PCT/US2005/044693 mailed Aug. 25, 2006.

*Primary Examiner* — Patrick Niland
(74) *Attorney, Agent, or Firm* — Brinks Hofer Gilson & Lione

(57) ABSTRACT

An environmentally safe additive and vehicle system are provided for water-based and oil-based printing inks, paints, coatings and adhesives which can be rapidly transferred, dispersed, dispensed, spread, dried and cured. The low cost, stable additive and vehicle system enhance multiple color, high speed printing with sharp, highly defined images and superior quality, and can be used on many different types of substrates, such as paper, paperboard, cardboard, clay coated board, foil, plastic, glass, metal, wood and composites. The additive may be formed by the reaction product of a photoinitiator, such as an UV-activated polyelectrolyte, and a monomer, such as an acrylate or a methacrylate in an aqueous solution. In other embodiments, the additive is formed from a carboxylic acid or anhydride and alkylalkanolamine monomer or a dialkylaminoalkyl acrylate or methacrylate monomer in an aqueous solution.

20 Claims, No Drawings

ADDITIVE AND VEHICLE FOR INKS, PAINTS, COATINGS AND ADHESIVES

The present patent document is a division of application Ser. No. 11/009,577, filed Dec. 10, 2004, now U.S. Pat. No. 7,863,485 which is hereby incorporated by reference.

TECHNICAL FIELD

The technical field of the invention is that of additives and vehicles for inks. The additives and vehicles may be used in waterborne inks for many types of printing, including flexographic, gravure, offset lithographic, and letterpress printing. The additives and vehicles may also be used in coatings, paints, and adhesives.

BACKGROUND

This invention pertains to aqueous polymeric compositions and, more particularly, to an additive and vehicle system for water based printing inks, paints, coatings and adhesives.

It is important to minimize, if not eliminate, volatile organic compound (VOCs) from paints, printing inks, coatings, and adhesives. Fumes emitted from such materials can be hazardous to the health and well-being of workers in paint manufacturing plants, printing companies, coating shops, and adhesive facilities. These fumes can be caused by flashing and vaporizing of solvents and free monomers. Furthermore, prolonged exposure to volatile emissions can impair the sight or brain function, and internal organs of people exposed to the volatile emissions. Some VOCs are also carcinogenic. It is often recommended that consumers using paints, printing inks, coatings, adhesives, and like materials, do so outside or in a well ventilated area to decrease health risks and injury. This is not always possible, particularly in wintertime or if the work is going to be done outside.

Not only can VOCs be injurious to the health and welfare of society, but specific amounts of VOCs are often prohibited or controlled by environmental laws. Moreover, products containing VOCs often cause waste disposal problems and expensive cleanup costs to comply with local anti-dumping ordinances and environmental regulations.

It is also desirable that printing inks, coatings, paints, and adhesives can be rapidly transferred, dispersed, dispensed, spread, and dried to increase throughput and production. This is especially important for four color printing on Gravure presses. Multiple color printing should have enough tack with yellow pigments to trap and avoid splattering of red pigments and subsequent dispersants. Furthermore, it is desirable that vehicles or carriers for printing inks, to coatings, paints and adhesives be rewettable or resolubilize so they do not stick to, gum up or clog printing presses and production equipment causing undesired downtime, decreased output, repairs and expense. Many conventional printing inks, paints, coatings, and adhesives become unstable during storage, which can lead to phase separation, layering, loss of quality, and delamination of the product.

Latex-based ink technology developed by Robert Slocombe is disclosed in U.S. Pat. Nos. 4,374,670 and 4,414,354. The Slocombe technology provided an approach which promised to solve some basic problems associated with waterborne inks and coatings. Among the promised benefits of the Slocombe technology were adhesion to low energy surfaces, high speed printing, and the ability to disperse most pigments.

The promise of the Slocombe technology was never realized for a number of reasons. The Slocombe technology centers around the high degree of free monomers which are present in Slocombe's product. The Slocombe technology is also limited to rubber-based resins. Slocombe's technology further needed to be activated by ultraviolet radiation which was not previously available. Slocombe's three component system had a limited pot life once the components were mixed together. Slocombe's inks further require a cosolvent to incorporate an initiator, polyelectrolyte and latex into a miscible solution. Moreover, Slocombe's cosolvents were unstable volatile organic solvents which are undesirable from an environmental viewpoint. Slocombe's polyelectrolyte interaction was also inefficient, and often amounted to 15%-25% of the resin formulation. These expensive compounds often resulted in inks which were too costly to be economically viable.

It is therefore desirable to provide an improved vehicle system for use in water-based printing inks, paints, coatings and adhesives, which avoids substantial use of solvents and volatile organic compounds, and overcomes most, if not all, of the preceding problems.

BRIEF SUMMARY

One embodiment is an additive that includes an aqueous solution of the reaction product of: (i) a first reagent including at least one material selected from the group consisting of a carboxylic acid and an anhydride, and (ii) a second reagent including at least one material selected from the group consisting of an alkyl alkanolamine monomer, a dialkylaminoalkyl acrylate monomer, and a dialkylaminoalkyl methacrylate monomer.

Another embodiment is an additive that includes an aqueous solution of the reaction product of (i) a first reagent including at least one material selected from the group consisting of a carboxylic acid containing a benzene ring and an anhydride containing a benzene ring, and (ii) a second reagent including at least one material selected from the group consisting of a dialkylaminoalkyl acrylate monomer and a dialkylaminoalkyl methacrylate monomer.

Another embodiment is a method of forming an additive, the method including forming an aqueous solution of a first reagent or a second reagent, and adding the other of the first reagent and the second reagent to the aqueous solution, wherein the first reagent includes at least one material selected from the group consisting of a carboxylic acid and an anhydride, and the second reagent includes at least one material selected from the group consisting of an alkylalkanolamine monomer, a dialkylaminoalkyl acrylate monomer, and a dialkylaminoalkyl methacrylate monomer, and wherein the first reagent and the second reagent react to form the additive.

Another embodiment includes a vehicle system that includes by weight: (a) about 4-45% of a first component, the first component including at least one material selected from the group consisting of an acrylic resin solution, a latex solution, a urethane solution, a microcrystalline wax solution, and a vegetable oil; (b) about 50-90% of a second component, the second component including at least one material selected from the group consisting of a fumaric resin solution and an acrylic resin emulsion; and (c) about 0.5-10% of an aqueous solution of an additive comprising the reaction product of (i) a first reagent comprising at least one material selected from the group consisting of a carboxylic acid and an anhydride; and (ii) a second reagent including at least one material selected from the group consisting of an alkyl alkanolamine monomer, a dialkylaminoalkyl acrylate monomer, and a dialkylaminoalkyl methacrylate monomer.

Another embodiment includes a vehicle system that includes by weight: (a) about 4-45% of a first component including at least one material selected from the group consisting of an acrylic resin solution, a latex resin solution, a paraffin solution, a paraffin emulsion, a urethane resin solution, and a vegetable oil; (b) about 50-90% of a second component including at least one material selected from the group consisting of a fumaric resin solution and an acrylic resin emulsion; and (c) about 0.5-10% additive in aqueous solution including the reaction product of (i) a first reagent including at least one material selected from the group consisting of a carboxylic acid containing a benzene ring and an anhydride containing a benzene ring; and (ii) a second reagent including at least one material selected from the group consisting of an alkylaminoalkyl acrylate monomer and an alkylaminoalkyl methacrylate monomer.

Another embodiment is a vehicle system including by weight: (a) about 80-99% of a first component including at least one material selected from the group consisting of an acrylic resin solution, a urethane resin solution, a latex resin solution, a latex resin emulsion, a wax dispersion or emulsion, a fumaric resin solution, and a vegetable oil; and (b) about 1-20% additive including in aqueous solution the reaction product of (i) a first reagent including at least one material selected from the group consisting of a carboxylic acid and an anhydride; and (ii) a second component including at least one material selected from the group consisting of a dialkylaminoalkyl acrylate monomer, a dialkylaminoalkyl methacrylate monomer, and an alkyl alkanolamine monomer.

An improved additive and vehicle system are provided which are particularly useful for water-based and aqueous polymer printing inks, paints, coatings and adhesives (bonding agents). The vehicle system containing the additive can also be used as a laminating adhesive, heat seal adhesive, bonding agent, or glue, such as a white glue. Advantageously, the improved additive and vehicle system substantially avoids the use or need of harmful solvents, free monomers, and volatile organic compounds (VOCs), such as isopropyl alcohol. The inventive additive and vehicle system can be used on numerous substrates, such as paper, paperboard, cardboard, clay coated board, foil, plastic, glass, metal, wood, and composites. Desirably, the additive and vehicle system are environmentally safe, economical, attractive, and effective.

Significantly, the inventive additive and vehicle system accelerates curing to allow for faster high quality printing. The additive and vehicle system also facilitate flocculation and VOC-free ink. When inks comprising a vehicle system containing the additive are transferred to a substrate such as paper, phase separation occurs and the polymer solid compounds adhere to the substrate. Liquid (e.g., water) is liberated, vaporized, and removed by air circulation and/or heat, and the coalesced polymer is cured. The vehicle system and additive are very stable, have a long shelf life, and can be made without a precursor. The vehicle system is particularly useful for waterborne or water-based systems and media with a pH between 7 and 14 and with less than 1% isopropanol.

To this end, the special vehicle system includes: (1) an acrylic resin solution; (2) a fumaric resin solution or an acrylic resin emulsion; and (3) an additive formed from a monomer and a carboxylic acid or anhydride, such as a photoinitiator. The vehicle system can also include: one or more of (4) a defoamer, (5) a surfactant, and (6) an inhibitor.

The acrylic resin solution can comprise an acrylic solution resin, water, and a diluent. The fumaric resin solution can comprise a fumaric resin, water, and a diluent. The acrylic resin emulsion can comprise an acrylic emulsion resin and water. The diluent can be a cutting agent such as ammonia, monoethanolamine (MEA), dimethylethanolamine (DMEA), triethanolamine (TEA), morpholine, propylene glycol and polypropylene glycol.

The monomer can be an acrylate or methacrylate, such as a dialkylaminoalkyl acrylate or methacrylate, for example, dimethylaminoethyl, diethylaminoethyl, or diethylaminopropyl acrylate or methacrylate. Alternatively, the monomer may be an alkyl alkanolamine monomer.

The carboxylic acid or anhydride, or photoinitiator, can be an ultraviolet responsive photoinitiator, such as 4,4'-carbonylbis(1,2-benzene-dicarboxylic acid); 3,3',4,4'-tetracarboxybenzophenone; 3,3',4,4'-benzophenonetetracarboxylic acid; benzophenonetetracarboxyldiphthalic acid; 4,4'-carboxydipthalic acid; benzophenonetetracarboxylic dianhydride; or orthobenzoylbenzoic acid. The photoinitiator may include a carboxylic acid or anhydride containing compound such as acrylic acid, benzoic acid, catechuic acid (3,4-dihydroxy benzoic acid), hydroxybenzoic acid, formic, acid, acetic, acid, propionic acid, oxalic acid, chloracetic acid, phthalic anhydride, salicylic acid, acetylsalicylic acid, 2,4-dichlorophenoxyacetic acid, acrylic acid, gluconic acid, adipic acid, maleic anhydride, fumaric acid, malonic acid, stearic acid, oleic acid, methacrylic acid, itaconic acid, sebacic acid, succinic acid, citric acid, tartaric acid, abietic acid, napthenic acid, palmitic acid, hydroxy acid, glycolic acid, lactic acid, ricinoleic acid (castor oil acid), maleic acid, protocatechoic acid, gallic acid, cinnamic acid, hydroxycinnamic, caffeic acid, or bile acid. Obviously, any processing that involves a photoinitiator must be accomplished in the absence of light, and the finished compounds are preferably kept out of the light and stored in dark or opaque containers.

In one preferred form, the monomer comprises dimethylaminoethyl methacrylate, the acrylic resin solution comprises a styrene acrylic copolymer, and the acrylic resin emulsion comprises a styrene acrylic copolymer emulsion.

In another embodiment, an additive useful in formulating inks, paints, coatings and adhesives includes an aqueous solution of carboxylic acid or anhydride compound, to which is added an alkylalkanolamine monomer, or a dialkyl alkanolamine acrylate or methacrylate monomer or dimer. Another embodiment includes a method of preparing the additive by forming an aqueous solution or slurry of the carboxylic acid or anhydride and slowly adding the amine or acrylate monomer or dimer. The amine or acrylate is added slowly to control the exotherm.

In another embodiment, an additive useful in formulating inks, paints, coatings and adhesives includes an aqueous solution of a benzene ring-containing carboxylic acid or anhydride compound, to which is added a dialkylaminoalkyl acrylate or methacrylate monomer or dimer. Another embodiment includes a method of preparing the additive by forming an aqueous solution or slurry of the benzene-ring containing carboxylic acid or anhydride and slowly adding the amine or acrylate monomer or dimer.

In another embodiment, an additive useful in formulating inks, paints, coatings and adhesives includes an aqueous solution of a carboxylic acid or anhydride compound, to which is added a alkyl alkanolamine acrylate or methacrylate monomer. Another embodiment includes a method of preparing the additive by forming an aqueous solution or slurry of the carboxylic acid or anhydride and slowly adding the acrylate monomer.

In another embodiment, an additive useful in formulating inks, paints, coatings and adhesives includes an aqueous solution of carboxylic acid or anhydride compound, to which is added an alkylalkanolamine monomer, or a dialkyoaminoalkyl acrylate or methacrylate monomer or dimer. Another embodiment includes a method of preparing the additive by forming an aqueous solution or slurry of the carboxylic acid or anhydride and slowly adding the amine or acrylate monomer or dimer.

The inventive vehicle system has produced unexpected surprisingly good results. A more detailed explanation of the invention is provided in the following description and claims.

DETAILED DESCRIPTION OF THE PRESENTLY PREFERRED EMBODIMENTS

A vehicle system substantially free of volatile compounds (VOCs) is formed for use in the manufacture of inks, coatings, paints, and by combining an additive with a first solution and a second solution or emulsion. The first resin solution may be an acrylic resin solution, a latex resin solution, or a vegetable oil resin solution. The second resin may be a fumaric resin solution or may be an acrylic resin emulsion.

A vehicle system additive comprising a non-VOC additive is added to the vehicle system to cause the other polymers to coalesce or to flocculate. The additive also assists in the rewetting of the vehicle.

A surfactant can be added to the vehicle system in order to reduce the liquid surface tension to almost that of solvent products or about 20 dynes/cm.

An inhibitor can be added to the vehicle system to prevent liquid ink from sticking in the cells of Gravure cylinders in the printing press. The inhibitor serves as a lubricant and also assists in the prevention of rust or oxidation of metal parts, in the printing press or other applicator. The inhibitor may also act to control coalescence of the ink or coating, i.e. to delay flocculation or phase separation, when slower drying or oxidation is desired.

As soon as the liquid of the vehicle system is applied to the substrate, in the presence of air, heat, or light, flocculation (phase separation) occurs and films are formed. The vehicle system is believed to provide two films. The first film causes the polymer to coalesce. The second film is protective and prevents fading of the ink, paint, etc. The liquid is liberated, vaporized or otherwise removed by air and/or heat. Unlike solvent based systems, the product (vehicle system) usually cures instead of dries.

The improved inventive vehicle system for aqueous polymer printing inks, paints, coatings and adhesives, includes by weight: 1-10% additive; 4-45% first acrylic resin solution; and 50-90% fumaric resin solution, or 50-90% acrylic resin emulsion. In a preferred form, the improved vehicle system comprises by weight: 2-6% additive; 15-35% acrylic resin solution; and 60-80% fumaric resin solution or 60-80% acrylic resin emulsion. Most preferably, for best results, the vehicle system comprises by weight: 2.5%-5% additive; 20-30% acrylic resin solution, and 65%-75% fumaric resin solution or 65-75% acrylic resin emulsion.

Instead of using the acrylic resin solution, excellent results are also obtained for a water-based ink when the vehicle system includes 4-45% latex or waterborne solution, 50-90% fumaric resin solution, and 2-5% additive. Examples of suitable waterborne resins include urethanes and paraffins. In another alternative, excellent results are obtained when the vehicle system includes 4-45% vegetable oil, 50-90% fumaric resin solution or acrylic resin emulsion, and 2-5% additive. Suitable vegetable oils include at least soybean oil and linseed oil. If a water-based paint is desired, good results may be obtained by using 5-10% of the additive, rather than a smaller amount, in formulations using acrylic resin, vegetable oil, latex, and urethanes as the first component. Coatings and adhesives may be formulated by substituting appropriate resins, primarily as the first component in the vehicle system. Emulsions of microcrystalline may also be used.

For paper substrates, fumaric resin compounds are preferably used in the vehicle system. For films and foil substrates, acrylic emulsion resins are preferably used in the vehicle system.

The vehicle system may also comprise by weight: a defoamer in an amount up to 1%, a surfactant in an amount up to 1%, an inhibitor in an amount up to 2%, and the vehicle system preferably comprises 0.05-0.15% defoamers, 0.05-0.15% surfactants, and 0.1-0.3% inhibitors. Since water-based printing inks have a tendency to foam, a defoamer is preferably added to the vehicle system on or before the vehicle system is put on a printing press, such as a Gravure printing press. A surfactant can be added to the vehicle system to decrease surface tension of the vehicle, increase transfer speed of the vehicle system from the applicator (e.g. printing press) to the substrate, enhance dispersion of the liquid and color dispersants (pigments), and improve spreading (trapping).

Advantageously, the vehicle system can be blended with almost any water-based color dispersion, ink or colorant that contains less than 1% isopropyl alcohol (isopropanol), and can run at over 2000 feet/min on a Gravure printing press.

Additive

An additive for a vehicle system solves the problem discussed above by replacing free monomers with an additive. This additive is unique in that it is water soluble and also allows it to be compatible with a wide variety of polymeric vehicle systems. The additive has also been found useful when mixed directly into already-formulated inks and coatings.

The vehicle system additive comprises a monomer and a carboxylic acid or anhydride compound. The monomer can be an acrylate or a methacrylate, such as dialkylaminoalkyl acrylate or methacrylate, for example, dimethylaminoethyl acrylate or methacrylate, diethylaminoethyl acrylate or methacrylate, or diethylaminopropyl acrylate or methacrylate. Alternatively, the monomer may be an alkylalkanolamine, such as N,N-dimethylethanolamine.

a. Aromatic and Non-Aromatic Carboxylic Acid or Anhydride-Containing Compounds.

The carboxylic acid or anhydride-containing compound is preferably a photoinitiator, such as an ultraviolet (UV) responsive photoinitiator, such as 4,4'-carbonylbis (1,2-benzenedicarboxylic acid); 3,3',4,4'-tetracarboxybenzophenone; 3,3'4,4'-benzophenonetetracarboxylic acid; benzophenonetetracarboxyldipthalic acid: 4,4'-carboxydipthalic acid; benzophenonetetracarboxylic dianhydride; and orthobenzoylbenzoic acid. The acid or anhydride may instead be a simpler carboxylic acid or anhydride containing compound such as benzoic acid, hydroxybenzoic acid, catechuic acid (3,4-dihydroxybenzoic acid), formic acid, acetic acid, propionic acid, oxalic acid, chloracetic acid, phthalic anhydride, salicylic acid, acetylsalicylic acid, 2,4-dichlorophenoxyacetic acid, acrylic acid, gluconic acid, adipic acid, maleic anhydride, fumaric acid, malonic acid, stearic acid, oleic acid, methacrylic acid, itaconic acid, sebacic acid, succinic acid, citric acid, tartaric acid, abietic acid, napthenic acid, palmitic acid, hydroxy acid, glycolic acid, lactic acid, ricinoleic acid, maleic acid, protocatechoic acid, garlic acid, cinnamic acid, hydroxycinnamic acid, caffeic acid, or bile acid.

In one preferred embodiment, the vehicle system additive comprises an aromatic amino salt, such as an aryl polyelectrolyte salt. Desirably, the salt comprising the vehicle system is a polyelectrolyte which is the reaction product of (1) a monomer; and (2) a photoinitiator that is a carboxylic acid containing compound. One preferred vehicle system comprises 2-benzophenone-carboxydimethylammoniumethylmethacrylate.

Advantageously, the vehicle system additive is safe, meets governmental standards and complies with environmental regulations. The vehicle system solves the problem discussed previously by replacing free monomers with a functional polyelectrolyte that provides a special vehicle system additive. This polyelectrolyte is unique in that it is stabilized as an amino salt which enables the polyelectrolyte to be water soluble and also allows it to be compatible with a wide variety of polymer systems.

It has been discovered that this additive is very stable in waterborne emulsions and waterborne solution resins which contain less than one percent isopropanol. It has also been discovered that this polyelectrolyte can be activated by heat alone from a convection oven as well as by UV radiation. A benefit of this technology is that it is effective in concentrations as low as one percent, whereas in the prior technology the polyelectrolyte often comprised 15 to 25% of the formulation.

The additive is manufactured by reacting the amino group in the monomer with a carboxylic acid or anhydride-containing compound. The resulting product is believed to be a quaternary ammonium compound prepared by reaction of a carboxylic acid or anhydride-containing compound and an amino-functional methacrylate or acrylate monomer, with the general formula:

wherein R is a "parent molecule," $COO^-$ is the reaction product formed from a carboxyl or anhydride group of the parent molecule, n is between 1 and 10, and is preferably 1 to 4. The $COO^-$ group or groups are derived from a functional group or reactive site on the parent molecule. An example is an acid, such as benzophenone carboxylic acid, benzoic acid; 4,4'bis (di-methylamino)-benzophenone; 2,2'4,6'-tetrahydroxy-benzophenone, isoeuxanthonic acid; 2,2',5,6'-tetrahydroxybenzophenone; euxanthonic acid; benzenecarboxylic acid; 1,4-benzenedicarboxaldehyde; terephthalaldehyde; 1,2-benzenedicarboxylic acid; 1,3-benzenedicarboxylic acid; isophthalic acid; 1,4-benzenedicarboxylic acid; terephthalic acid; 2-aminobenzeneboronic acid; 2-amino-1,3-benzenedicarboxylic acid; 1,3-benzenedicarboxylic acid; 4-bromo-1,3-benzenedicarboxylic acid; 2-chloro-1,3-benzenedicarboxylic acid; 4,6-dichloro-1,3 benzenedicarboxylic acid; 2,5-dichloro-1,3-benzenedicarboxylic acid; 4,5-dimethoxy-1,3 benzenedicarboxylic acid; 2-nitro-1,3-benzenedicarboxylic acid; tetrabromo-1,3-benzenedicarboxylic acid; benzenepentacarboxylic acid; 4,4'-carbonylbis (1,2-benzene dicarboxylic acid); 3,3',4,4'-tetracarboxybenzophenone; 3,3'4,4'-benzophenonetetracarboxylic acid (BTA); 4,4'-carbonyldiphthalic acid; benzophenonetetracarboxylic dianhydride; orthobenzoylbenzoic acid; or methanone benzoic acid; and is benzophenone in a preferred embodiment of the product. Benzophenone is also referred to as diphenylketone and has a formula of $(C_6H_5)_2CO$.

Benzophenone is partially soluble in alcohol and ether. Benzophenone can be used as an ultraviolet absorber for polymerization or as an inhibitor. In a mono-functional photoinitiator such as benzophenone, n in the above formula is one; in a tetra-functional photoinitiator, such as BTA, n may be from one to four, depending on the stoichiometry of the mixture and the degree of completion desired. Mono-anhydrides may have two functional attachment sites. For instance, when using the additive will be more basic if more of such alkylamino acrylates or methacrylates are added, and will more acidic if fewer are added.

b. Dialkylaminoalkyl Acrylate or Methacrylate Monomer $N^+$—H—R',R",R"' is a quaternary ammonium component or salt formed from a substituent of a dialkylaminoalkyl acrylate or methacrylate monomer, a compound that contains an amino functional group. In what is believed to be an acid-base reaction with the carboxylic acid or anhydride compound or photoinitiator, the acid furnishes the fourth group for the quaternary ammonium compound, a hydrogen ion or proton. The N is a nitrogen atom from the dialkylaminoalkyl acrylate or methacrylate monomer, the R' group is an alkyl acrylate or methacrylate, and the R" and R"' can be hydrogen, a dialkylaminoalkyl acrylate or methacrylate, or a saturated or unsaturated carbon group such as an alkyl, aryl, arylalkyl, alkane, alkene, alkadiene, napthene, or cycloolefin. The $N^+$—H—R',R",R"' component can be derived, for example, from N,N-dialkylaminoalkyl acrylate or N,N-dialkylamino-alkyl methacrylate, such as N,N-dimethylaminoethyl acrylate, N,N-dimethylaminoethyl methacrylate (MAME) or (DMAEMA); N,N-diethylaminoethyl acrylate; N,N-diethylaminoethyl methacrylate; N,N-diethylaminopropyl acrylate; N,N-diethylaminopropyl methacrylate; dimethylethylaminobutyl acrylate; or dimethylaminobutyl methacrylate.

Polyelectrolytes are high polymer substances either natural (protein gum arabic) or synthetic (polyethyleneimine, polyacrylic acid salts) containing ionic constituents. They may be cationic or anionic. Water solutions of both types are electrically conductive. In a polyelectrolyte, ions of one sign are attached to a larger molecule or polymer chain while those of the opposite sign are free to diffuse into the solution. Polyelectrolytes are organic flocculants. A flocculent is a substance that induces flocculation. R" and R"' can be hydrogen, one or more of the polyelectrolyte listed above, or saturated or unsaturated carbon groups, such as alkyl, aryl, arylalkyl, alkanes, alkanes, alkenes, alkadienes, napthenes, and cycloolefins. In the preceding formula, n is a number from 1 to 10, and is preferably 1 to 4. The acidity or basicity (pH) of the additive may be tailored by tailoring the stoichiometry of the acid/anhydride compound and the monomer used.

When mixing the components of the additive, it is important to keep the temperature low, preferably well below room temperature. In this manner, only the amine portion of the monomer will react with the acid or anhydride, leaving the acrylate or methacrylate function available for later reactions, such as flocculation. In addition to dialkylaminoalkyl acrylate or methacrylate monomer, other monomers may also be used, such as alkyl alkanolamine monomers. Examples are N,N-diethylethanolamine, N,N-dimethylethanolamine, N-methyl-N-ethylethanolamine, and N-methyl-diethanolamine The additive is very stable in waterborne emulsions and waterborne solution resins which contain less than 1% isopropyl alcohol, and very low solvent contents in general. The technology preferably requires that the pH of waterborne systems be between 7 and 10 with the most preferred pH to be about 8 to 9.5. A benefit of this technology is that it is effective in concentrations as low as 1%, whereas in the prior technology the polyelectrolyte often comprised 15 to 25% of the formulation.

One useful photoinitiator is aromatic polycarboxylic acid having the formula $C_{17}H_{10}O_9$ with a weight of 358.26 g/mol, particularly 4,4'-carbonylbis (1,2-benzene dicarboxylic acid); 3,3',4,4'-tetracarboxybenzophenone; 4,4'-carbonyldipthalic acid; 3,3'4,4'-benzophenone-tetracarboxylic acid, known as BTA, such as sold under the product name Allco BTA by Allco Chemical Corporation of Galena, Kans. BTA has a melting point of 215-230° C. BTA dehydrates to form dianhydride near the melting point. BTA has a boiling point of 380-400° C. as a dianhydride. BTA has a bulk density of 0.51 kg/L (32 lbs/ft$^3$) (dry powder) and a specific gravity of 1.46 at 26° C./20° C. BTA has a pH of 2.4 at 2.3 g/L (20° C.) and has a solubility in water of 0.3 g/100 g at 26° C.

One useful polyelectrolyte methacrylate monomer is dimethylaminoethylmethacrylate, known as MAME or DMAEMA, such as that sold by Allied Colloids Inc. of Suffolk, Va., also sold by Degussa. DMAEMA has a boiling point of 190° C., a vapor density of 5.4, a specific gravity of 0.93, a vapor pressure of <1 at 26° C., and a flashpoint of 67° C. DMAEMA is a clear liquid with mild amine-like odor and is soluble in water. When BTA is used as the photoinitiator with DMAEMA, the resulting additive has no free monomers or only trace amounts of free monomers, i.e. less than 50 ppm. BTA produces better results than benzophenone tetracarboxylic dianhydride (BTDA).

Acrylic Resins

The term "acrylic" designates products obtained by the polymerization of esters of acrylic ($H_2C:CHCOOH$) or methacrylic acid ($H_2C:C(CH_3)COOH$). These acids, and their nitrites and esters, are all included in the acrylic group. In addition to their clarity and unusual optical properties, acrylics generally have a low specific gravity, low water absorption, high dielectric strength, and good shock resistance.

Acrylic resins are thermoplastic polymers or copolymers of acrylic acid, methacrylic acid, or esters of these acids. Methylmethacrylate is an acrylic resin monomer that can be copolymerized with other methacrylate esters and many other monomers. Aqueous dispersions of polymethylmethacrylate can be used in water based paints. Solutions of polymethylmethacrylate in organic solvents can be used in protective coatings and light colored automobile lacquers.

Polymethylmethacrylate and methyl methacrylate have been produced under the brand names and trademarks of: (a) Plexiglas by Rohm & Haas Co. of Philadelphia, Pa., and (b) Lucite by E.I. du Pont de Nemours & Company of Wilmington, Del. Other companies also manufacture polymethylmethacrylate and methyl methacrylate.

Monomeric methylacrylate can be produced by the reaction of aqueous methyl alcohol with ethylene cyanohydrin which can be obtained by the reaction of ethylene oxide and hydrogen cyanide. Ethylacrylate can be produced continuously by the addition of excess ethyl alcohol to acetylene in the presence of hydrogen chloride and nickel carbonyl. Monomeric methylmethacrylate can also be prepared from acetone cyanohydrin or by the esterification of methacrylic acid with methanol in the presence of phosphorus pentoxide. The methacrylic acid can be obtained by the catalytic oxidation of methacrolein which in turn is produced by the vapor phase catalytic oxidation of methyl alcohol.

Polyacrylic and polymethacrylic acid can be produced by addition type polymerization of the monomeric acids or by saponification of the polymeric esters. These acids and their sodium salts are water-soluble and are used as thickening agents in water-based paints and printing inks. The copolymer of ethylacrylate and 2-chloroethyl vinyl ether or 2-chloroethylacrylate can be cured by heating to give these materials excellent resistance to hot oils and oxidative degradation. Poly-1,1-hydroperfluorobutyl acrylate, a commercially available elastomer, has excellent resistance to hot solvents and thermal and oxidative degradation. Methylcyanoacrylate is an effective adhesive since it polymerizes in the presence of moisture or alcohol.

Acrylic Resin Solution

The acrylic resin solution can comprise, by weight, 20-50% acrylic solution resin, 0-75% water, and 0-20% of an amine-containing, acrylic-cutting diluent, and preferably includes 25-45% acrylic solution resin, 45-65% water, and 1-10% amine-containing acrylic-cutting diluent. For best results, the acrylic resin solution comprises, by weight, 30-40% acrylic resin, 50-60% water, and 2-8% amine-containing, acrylic-cutting diluent. The acrylic solution resin preferably have an acid number of at least 180. The amine containing, acrylic-cutting diluent can comprise monoethanolamine (MEA), dimethanolamine (DMEA), triethanolamine (TEA), morpholine, propylene glycol, polypropylene glycol, and preferably comprises ammonia (NH3) for best results.

The acrylic solution resin is preferably a styrene acrylic copolymer, such as that sold by the Noveon, Inc., of Cleveland Ohio, under the trade name CARBOSET GA-1931. CARBOSET GA-1931 is a solution of acrylic copolymer in ammonia water, is 100% soluble in water, and has a boiling point of 100° C., a freeze point of 0° C. at a specific gravity of 1.1-1.2, a vapor pressure of 17 mm Hg, and a vapor density of 0.62. CARBOSET GA-1931 contains less than 1% ammonia, less than 0.7% acrylic acid, less than 0.1% styrene, and less than 1% isopropyl alcohol. CARBOSET GA-1931 has the following properties: total solids of 41% by weight and 34.5% by volume; a pH of 8.5-9.2; a viscosity of 5000 cps (Brookfield at 25° C.); 9 lbs per gallon, a volatile organic content (VOC)<1%; and an acid number on solids of 190. CARBOSET GA931 is easy to handle, has high gloss, exhibits excellent pigment wetting, gloss and resolubility, enhances flow and leveling, and is an outstanding pigment dispersant.

Other acrylic solution resins from Noveon, Inc. are also useful. These include the solutions sold under the trade names CARBOSET GA-1926, CARBOSET GA-1993, CARBOSET XPD-2091. CARBOSET GA-1926 is an acrylic copolymer in ammonia water. CARBOSET GA-1993 is a styrene/acrylic copolymer in water with neutralized ammonia, and contains no less than 1% ammonia and less than 0.05% styrene. CARBOSET XPD-2091 comprises 45-55% acrylic polymer, 45-55% water, <0.01% acrylic acid, <0.01% styrene, and <0.1% isopropanol. CARBOSET XPD-2091 is 100% soluble in water. Acrylic copolymer resins can be useful, such as those also sold by Noveon, Inc., of Cleveland Ohio, under the trade names CARBOSET GA-1161 and CARBOSET GA-1162.

Other acrylic solution resins can be useful, such as those sold by Johnson Polymer Co. of Sturtevant, Wis., under the trade name JONCRYL 60 and 134 (Product Code 16540-5). JONCRYL 134 (Product Code 16540-5) comprises by weight: 30-40% styrene acrylic polymers, 60-70% water, 1-2% ammonium hydroxide, 1-55 urea, 1-3% polyoxyethylene block copolymer, and <0.99% styrene.

Other acrylic resins may be useful, such as those sold by Rohm & Haas, of Philadelphia, Pa., under the trade name MORCRYL 134 comprising a styrene acrylic solution. MORCRYL 134 has a pH of 8.5, a vapor density of 1, a vapor pressure of 33 at 200° C., a specific gravity of 1; and a boiling point of 82° C.

Latex Resins

Latex or waterborne resins may be used in formulating a vehicle in embodiments of the present invention. A latex is generally defined as a water solution or emulsion (waterborne) of a synthetic rubber or plastic obtained by polymerization, and may also include natural or urethane solutions or emulsions. For instance, a number of emulsions, primarily of microcrystalline waxes are available for commercially for ink and coating formulations. These waxes tend to be hydrocarbon-based, such as polyethylene, polypropylene, or generally alkane or paraffin-based, and combinations of one or more of polyethylene, polypropylene, and paraffin waxes. One example is the Jonwax line of microcrystalline waxes available from Johnson Polymer, Inc., Sturtevant, Wis. The wax particles in these emulsions may range from 50 to 4000 nm, and the solids loadings may vary considerably, at least from about 25 to 50 percent solids. Jonwax 4 and Jonwax 26 are two examples of waterborne waxes or resins that may be used in embodiments of the present invention. Jonwax 26 has a 26% solids loading of a polyethylene wax dispersion having an average particle size of 53 nm. Jonwax 4 has a 40% solids loading of a polyethylene was dispersion having an average particle size of 4000 nm. These waterborne resins are well-known to those in vehicle arts for providing rub and scuff resistance in water-based ink formulations. They may also be used in vehicles for other coatings, such as scuff-resistant paints.

Urethane Resin Solution

In some circumstances, it may be desirable to use waterborne resins made from other chemical systems. For example, we have tested several waterborne urethanes as part of the first component of a vehicle system, the first component generally including one of an acrylic resin solution, a latex resin solution, a vegetable oil, or a urethane. In one embodiment, urethane resins in the form of aqueous dispersions are useful. For instance, urethane dispersions containing from 30 to 51 percent solids are available from a number of vendors. We have successfully used at least Joncryl U4100 and U4188 (containing respectively, 33 and 38 percent solids), from Johnson Polymer, Inc., Sturtevant, Wis., in formulating paint vehicles. A number of other grades are also available from this and other vendors. The urethanes are especially helpful in formulating inks that allow dispersion of pigments in lower loading. If urethanes are used, it is preferable that they have very minimal amounts of m-pyrrol and methylpyrrolidine.

Vegetable Oils

We have also discovered that vegetable oils may be used to prepare vehicles for inks, paints, and coating in embodiments of the present invention. For example, linseed oils and oils made from soy may be used. A variety of pale and dark linseed oils are available from a number of vendors. We have found that linseed oils from the Lawter International, Inc., of Pleasant Prairie, Wis., are suitable. Grades SR0000 to SR3, in Dark and Pale grades, are highly useful, the dark grades having a Gardner-Holdt color of 15 and the pale oils having a Gardner-Holdt color of 10. All grades have an acid value of about 15 and a density of about 7.9 lb/gallon. In the dark grades, viscosity varies from 70 to 5300 cp, while in the pale grades, viscosity ranges from 110 to 6900 poises, all readings taken at 25° C. (77° F.). This range allows the user to tailor the viscosity of the vehicle as desired. As is well known to users, offset lithographic and letterpress inks tend to be much more viscous or pasty than inks suitable for flexographic or gravure use. Thus, linseed oils in particular may be used to help adjust the viscosity of the vehicle to the desired range. Clearly, the linseed oils are very useful in the higher viscosity ranges, as well as providing grades for the very low viscosity ranges. The fact that soybean oils are sourced from a renewable source and are available world-wide is helpful in considering their logistics for manufacture and sales everywhere.

Vegetable oils are typically fatty acids with a broad mixture of carbon-chain lengths and degrees of unsaturation, usually with one, two or three carboxylic acid groups. Soybean oil, for instance typically has about 10-19% saturated fat (mostly $C_{16}$ and $C_{18}$) with a single carboxylic acid function, about 22-34 percent unsaturated $C_{18}$ with a single carboxylic acid functionality, and 50-60 percent unsaturated $C_{18}$ with two carboxylic acid groups and 2-10 percent unsaturated $C_{18}$ with three carboxylic acid groups. Other vegetable oils have a constituency that is similarly varied in terms of both unsaturation, molecular weight, and acid functionality. Accordingly, care should be paid to the stoichiometry of the particular batch that is used when preparing the additive for use in embodiments of the present invention. Other vegetable oils that may be used include, without limitation, corn oil, cottonseed oil, olive oil, palm oil, palm kernel oil, peanut oil, linseed oil, tall oil, and tung oil.

Soybean oils may also be used, preferably refined soybean oils with impurities and undesirable portions removed. Soybean oils are available from a variety of refiners, including Cargill, Inc., Minneapolis. Minn. Preferred is the technical grade soybean oil. In order for easy processing, the oils are preferably degummed, refined, bleached and deodorized. Other oils may also be used, such as tung oil, tall oil, and other vegetable oils well-known to those in art of preparation of vehicles for inks, coatings, and paints.

Fumaric Resin Solution

The fumaric resin solution can comprise, by weight, 20-0% fumaric resin, also referred to as a fumaric solution resin, 0-75% water, and 0-30% of an amine containing, fumaric-cutting diluting agent (diluent), and preferably comprises 25-45% fumaric resin, 45-65% water, and 5-15% of an amine-containing, fumaric-cutting diluting agent. For best results, the fumaric resin solution comprises 30-40% fumaric resin, 50-60% water, and 8-12% amine-containing, fumaric-cutting diluting agents. Fumaric resin is derived from pine tar. The preferred fumaric resin has an acid value of 120-300 and most preferably has an acid value of at least 60.

The amine-containing, fumaric-cutting diluting agent can include dimethanolamine (DMEA), triethanolamine (TEA), ammonia, morpholine, propylene glycol, polypropylene glycol, and preferably comprises monoethanolamine (MEA) for best results. The amine ratio of the diluents of monoethanolamine (MEA) in the fumaric solution resin to ammonia (NH3) in the acrylic solution resin can range from 1:1 to 10:1, preferably from 3:1 to 6:1 for best results.

One preferred type of fumaric resin is sold by Akzo Coatings, Inc of Baxley, Ga. under the trade name of FILTREZ 5014. FILTREZ 5014 is a fumaric modified glycerol ester of rosin, and has a softening point of 135-140° C. (R & B), an acid value of 160-180, a product density of 9.9 lbs/gal., a VOC content of <1%, and a flash point of 425° F. (218° C.). Other fumaric resins may also be useful, such as grades FP 130, FP 171 and FP 300, also available from Akzo Nobel.

Other fumaric resins can be useful, such as sold by AKZO Coatings, Inc of Baxley, Ga. under the trade names of FILTREZ 643. FILTREZ 643 is a solution of resin modified polymers and hydrocarbon resin, and has a VOC content <1%. Other fumaric resins from other producers may also be useful.

Acrylic Resin Emulsion

The acrylic resin emulsion can comprise, by weight, 50-100% acrylic emulsion resin and 0-30% water, and preferably comprises 60-90% acrylic emulsion resin and 5-25% water. For best results, the acrylic resin emulsion is 75%-85% acrylic emulsion resin and 10-20% water. The acrylic resin emulsion preferably comprises a dispersion of styrene acrylic copolymer emulsion in water, such as sold by Noveon, Inc, of Cleveland, Ohio, under the trade names CARBOSET GA-1086 and CARBOSET GA-1087. CARBOSET GA-1086 and GA-1087 contain less than 0.5% acrylic acid, less than 0.25% isopropyl alcohol, and less than 0.05% styrene, and have the following properties: 48-49% total solids by weight, a pH of 8.6; a glass transition temperature of 40° C. and 105° C., respectively; a viscosity of 650-800 cps at 25° C. (Brookfield); and an acid number on solid of 50. CARBOSET GA-1086 and GA-1087 are translucent, high gloss and fast drying. CARBOSET GA-1086 exhibits excellent adhesion to various substrates including flexible films and non-porous material and are water resistant. CARBOSET GA-1087 has excellent alcohol compatibility and is useful for inks and varnishes for paper and paperboard.

Other acrylic emulsion resins can be useful, such as others sold by Noveon, Inc. under the trade names CARBOSET GA-1166, CARBOSET GA-1161, and CARBOSET GA-1162. CARBOSET GA-1166 is a styrene acrylic copolymer dispersion in ammonia water, is soluble in alkaline water, and has the following properties: a pH of 8.2 9.2, a boiling point of 100° C. a vapor pressure of 17, a freeze point of 0° C., a vapor density of 0.62, and a specific gravity of 1.05 to 1.1. CARBOSET GA-1161 and CARBOSET GA-1162 can also be formulated into acrylic to copolymer emulsion resins. Other acrylic emulsion resins can be useful, such as those sold by Johnson Polymer Co. of Sturtevant, Wis., under the trade names JONCRYL 77 and 89. JONCRYL 89 (Product Code 16360-4-6). JONCRYL 89 (Product Code 16360-4-6) comprises by weight: 40-50% styrene acrylic polymers, 2-3% ammonium hydroxide, <2% polypropylene glycol, and <0.2% styrene. Other acrylic emulsion resins may also be useful.

Defoamers

A defoamer is useful to reduce the foam in water based systems. A defoamer is preferably added to the vehicle system on or before the vehicle is put on a printing press. One preferred defoamer comprises a fluorochemical anionic surfactant, such as sold by 3M Industrial Chemical Products Division of the 3M Company of St. Paul, Minn. under the trade name FC-129. This product is believed to be no longer available.

Other defoamers can be useful such as those sold by Tego Chemie Service USA, a division of Goldschmidt Chemical Corp., of Hopewell, Va., under the trade names TEGO Foamex 3062, TEGO Foamex 800, and TEGO Foamex 810. TEGO Foamex 3062 is a hydrophobic polysiloxane polyether copolymer. TEGO Foamex 3062 has a density of 1 g/cc at 200° C., a flash point of 100° C., and a weight of 8.3 lbs per gallon. TEGO Foamex 800 is an emulsion of a hydrophobic polysiloxane polyether copolymer. TEGO Foamex 800 is useful for water-based paints, and has a density of 1 g/cc at 25° C., a viscosity of 600 cps, and a freezing point of 0° C.

Other defoamers useful for suppressing and minimizing foam are silicon-based defoamers comprising polydimethylsiloxane that contains 10% active silicone, such as produced under the brand name SAG 10 antifoam by Univar Corp., of Seattle, Wash., USA. Other defoamers can also be useful, such as the following antifoam emulsions and compounds produced by Univar: SAG 30 (30% active silicone), SAG 5 693 (polyalkylene glycol/silicone), SAG 413 0, SAG 4220, SAG 544 1, SAG 710 and SAG 730.

Other defoamers can be useful such as those sold by Air Products and Chemicals, Inc of Allentown, Pa., under the brand names SURFYNOL DF-695 and SURFYNOL DF-75. SURFYNOL DF-75 is useful for water-based formulations in systems based upon acrylic resins, such as for aqueous inks, overprint varnishes, coatings, and adhesives. SURFYNOL DF-75 has a specific gravity of 0.99, a pH of 8, a boiling point of 121° C., and a flash point of >204° C. SURFYNOL DF-695 is a silicone-based emulsion defoamer and is useful in aqueous ink systems. SURFYNOL DF-695 has a specific gravity of 1.01 to 1.04, a pH of 7.3, a viscosity of 9000 cps at 25° C., and a boiling point of 100° C.

Inhibitors

An inhibitor can be used for vehicle transfer, storing and shipping to prevent spontaneous, rapid and undesired polymerization, as well as to prevent corrosion. An inhibitor can be added to the vehicle system to prevent liquid ink from sticking in the cells of Gravure cylinders in the printing press. The inhibitor also serves as a lubricant. The inhibitor further assists in the prevention of rust or oxidation of metal parts, in the printing press or other applicator.

One preferred inhibitor comprises acid phosphate/diethylamine salts, such as sold by Rhodia, Cranbury, N.J., under the trade name VIRCO PET 40. VIRCO PET 40 comprises by weight: 30% phosphoric acid, mono-(2-hexyloxyethyl) ester, bis(diethylamine) salts; 60% phosphoric acid, bis (2-hexyloxyethyl) ester, diethylamine salts; and 10% diethylamine. Other inhibitors from Rhodia include VIRGO PET 30. VIRGO Pet 30 is a mixture of a hydrogen phosphate compound, 2-butoxy ethanol, and other ingredients. These inhibitors may be thought of as coalescing agents, in the sense that they act to delay coalescence of the solution. This may be useful for prolonging the pot life or drying time of architectural coatings or other products where desired. For instance, a user may wish to touch up a paint or a coating before it cures so that the finished product has a smooth, uniform appearance.

Surfactants

A surfactant can be added to the vehicle system to decrease surface tension of the vehicle, increase transfer speed of the vehicle from the applicator (e.g. printing press) to the substrate, enhance dispersion of the liquid and color dispersants (pigments), and improve spreading (trapping).

Anionic fluorochemical surfactants or fluorocompound wetting agents can also help provide excellent adhesion of the product (vehicle system) to the substrate. Some useful fluorosurfactants or fluorocompound wetting agents are those sold by 3M Company of St. Paul, Minn., under the FLUORAD brand names FC-4430 and FC-4432. These are believed to be polymeric, non-ionic surfactants. Fluorosurfactants can be used alone or with a hydrocarbon surfactant.

A caustic coupling surfactant, such as those sold by BASF Corporation, Mount Olive, N.J., under the brand name Mazon 40, can also be useful in some circumstances. Mazon 40 is a nonionic surfactant which is soluble in water as well as in liquid caustic and other highly alkaline solutions. Mazon 40 has a specific gravity of 1.15 at 25° C., a boiling point of 100° C., and a flash point of >93.3° C.

Other nonionic surfactants that can be useful are ethoxylated surfactants comprising ethoxylated acetylenic diols or ethoxylated tetramethyldecynediol, such as those sold under the brand names SURFYNOL 465 and SURFYNOL 485 by Air Products and Chemicals, Inc. of Allentown, Pa. SURFYNOL 465 and SURFYNOL 485 provide defoaming nonionic surfactants and have a pH of 6-8. SURFYNOL 465 and SURFYNOL 485 exhibit good wetting performance in paints, coatings, inks, adhesives, and emulsion polymerization. SURFYNOL 465 contains 65% ethylene oxides by weight and has a specific gravity of 1.038, a viscosity of <200 cps at 20° C., and a pour point of 6.67° C. SURFYNOL 485 contains 85% ethylene oxides by weight and has a specific gravity of 1.08, a viscosity of <350 cps at 20° C., and has a pour point of 29° C.

Other fluorosurfactants can be useful surfactants, such as those sold by E.I. DuPont de Nemours & Company of Wilmington, Del., USA under the ZONYL brand names FSP, FSE, FSJ, FSN, FSN-100, FSO, and FSO-100.

ZONYL FSO is a fluorinated surfactant comprising 50% telomer B monoether with polyethylene glycol, 25% ethylene glycol, 25% water, has a boiling point of 100° C., a vapor density of 2.1, a specific gravity of 1.3 and is 50% volatile. ZONYL FSP is a fluorinated surfactant including 20% isopropyl alcohol, 40-45% water and the balance telomer B phosphate ammonium salt, with a specific gravity of 1.15, a pH of 6-8, and is 65% volatile. ZONYL FSN is a fluorinated surfactant with about 40% fluorosurfactant, 30% isopropyl alcohol, 30% water, a flash point of 22° C. (72° F.) (Pensky Martens closed cup method), a specific gravity of 1.06, a pH of 7.5-8.5, and is 60% volatile.

Nonionic surfactants are surface active compounds which do not ionize in a water solution. Oftentimes, these surfactants possess hydrophilic characteristics by virtue of the presence therein of an oxygenated chain (e.g., a polyoxyethylene chain), the lyophilic portion of the molecule being derived from fatty acids, phenols, alcohols, amides or amines. Exemplary compounds are the poly(ethylene oxide) condensates of alkyl phenols, e.g. the condensation product formed from one mole of nonylphenol and ten moles of ethylene oxide, and the condensation products of aliphatic alcohols and ethylene oxide, e.g. the condensation product formed from 1 mole of tridecanol and 12 moles of ethylene oxide.

The nonionic surfactants can comprise phenol ethoxylates comprising a condensate product of ethylene oxide and an alkyl phenol or an aliphatic alcohol. The nonionic surfactants preferably comprise nonylphenol ethoxylate such as T-DET-N, and/or octylphenol ethoxylate. The nonionic surfactants are reaction products of ethylene oxide and nonylphenol and/or octylphenol. The ratio of the phenol to the ethylene oxide can range from 2:20 to 4:16, and preferably is about 8:12.

Nonionic synthetic surfactants can comprise nonionic detergents. Nonionic synthetic surfactants can also be formed by condensing ethylene oxide with a hydrophobic base formed by the condensation of propylene oxide with propylene glycol. The hydrophobic portion of the molecule which, of course, exhibits water solubility has a molecular weight of about 1200 to 2500. The addition of polyoxyethylene radicals to this hydrophobic portion tends to increase the water solubility of the molecule as a whole and the liquid character of the product can be retained up to the point where polyoxyethylene content is about 50% of the total weight of the condensation product.

Other nonionic synthetic surfactants can include the polyethylene oxide condensates of alkylphenols, e.g. the condensation products of alkyphenols or dialkylphenols wherein the alkyl group contains from about 6 to 12 carbon atoms in either a straight chain or branched chain configuration, with ethylene oxide. The ethylene oxide can be present in amounts equal to 8 to 25 moles of ethylene oxide per mole of alkylphenol. The alkyl substituent in such compounds 15 can be derived from polymerized propylene, diisobutylene, n-octene, or n-nonene.

Nonionic surfactants can also be produced from the condensation of ethylene oxide with the reaction product of propylene oxide and ethylenediamine, e.g. compounds containing from about 40% to about 80% polyoxyethylene by weight and having a molecular weight of from about 5,000 to about 11,000 resulting from the reaction of ethylene oxide groups with a hydrophobic base comprising the reaction product of ethylenediamine and excess propylene oxide; the base having a molecular weight on the order of 2,500 to 3,000.

Other nonionic surfatants include the condensation product of aliphatic alcohols having from 8 to 18 carbon atoms, in either straight chain or branched chain configuration, with ethylene oxide, e.g. a coconut oil alcohol ethylene oxide condensation product having from 10 to 30 moles of ethylene oxide per mole of coconut alcohol, and the coconut alcohol fraction having from 10 to 14 carbon atoms.

Further nonionic surfactants include long chain tertiary amine oxides corresponding to the following general formula: $R_1R_3R_2N \rightarrow O$, wherein $R_1$, is an alkyl radical of from about 8 to 18 carbon atoms, and $R_2$ and $R_3$ are each methyl or ethyl radicals. The arrow in the formula is a conventional representation of a semi polar bond. Examples of amine oxides suitable for use include dimethyldodecyl-amine oxide, dimethyloctylamine oxide, dimethyldecylamine oxide, and dimethylhexadecylamine oxide.

Other nonionic surfactants can include long chain tertiary phosphine oxides corresponding to the following general formula: $RR'R''P \rightarrow O$, wherein R is an alkyl, alkenyl or monohydroxyalkyl radical ranging from 10 to 18 carbon atoms in chain length, and R' and R" are each alkyl or monohydroxyalkyl groups containing from 1 to 3 carbon atoms. The arrow in the formula is a conventional representation of a semi polar bond. Examples of suitable phosphine oxides are: dimethyldodecylphosphine oxide, dimethyltetradecylphosphine oxide, ethylmethyltetradecylphosphine oxide, cetyl dimethylphosphine oxide, dimethylstearylphosphine oxide, cetylethylpropylphosphine oxide, diethyldodecylphosphine oxide, diethyltetradecylphosphine oxide, dipropyl-dodecylphosphine oxide, bis(2-hydroxymethyl)dodecylphosphine oxide, bis(2-hydroxyethyl)-dodecylphosphine oxide, (2-hydroxypropyl)methyltetradecylphosphine oxide, dimethyldodecylphosphine oxide, and dimethyl-2-hydroxydodecylphosphine oxide.

It may be useful to use other surfactants, such as an anionic surfactant, a cationic surfactant, an ampholytic surfactant or a zwitterionic surfactant. The anionic surfactants comprise surface active compounds. The anionic surfactants can contain hydrophilic and lyophilic groups in their molecular structure which ionize in an aqueous medium to give anions containing the lyophilic group. Typical of these compounds are the alkali metal salts of organic sulfonates or sulfates, such as the alkali metal alkyl aryl sulfonates and the alkali metal salts of sulfates of straight chain primary alcohols. Sodium dodecylbenzene sulfonate and sodium lauryl sulfate are typical examples of these anionic surface active compounds.

Anionic surfactants can comprise synthetic detergents. Anionic surfactants can include sodium alkyl sulfates, especially those obtained by sulfating the higher alcohols ($C_8$ to $C_{18}$ carbon atoms) produced by reducing the glycerides of tallow or coconut oil; sodium alkylglycerylethersulfonates, especially those ethers of the higher alcohols derived from tallow and coconut oil; sodium coconut oil fatty acid monoglyceride sulfates and sulfonates; the reaction product of fatty acids esterified with isethionic acid and neutralized with sodium hydroxide, where, for example, the fatty acids are derived from coconut oil; sodium or potassium salts of fatty acid amide of a methyltauride in which the fatty acids are derived from coconut oil.

The cationic surfactants can include cationic detergents. The cationic surfactants comprise compounds which ionize in an aqueous medium to give cations containing the lyophilic group. Typical of these compounds are the quaternary ammonium salts which contain an alkyl group of about 12 to 18 carbon atoms, such as lauryl benzyl dimethyl ammonium chloride.

Ampholytic surfactants are compounds having both anionic and cationic groups in the same molecule. Exemplary of such compounds are derivatives of aliphatic amines which contain a long chain of about 8 to 18 carbon atoms and an anionic water solubilizing group, e.g., carboxysulfo, sulfo or sulfato. Examples of ampholytic detergents are: sodium-3-dodecylaminopropane sulfonate, sodium-N-methyl laurate, and related substances such as higher alkyl disubstituted amino acids, betaines, sulfated long chain olefinic amines, and sulfated imidazoline derivatives.

Zwitterionic surfactants can include synthetic detergents. Zwitterionic surfactants are generally derivatives of aliphatic quaternary ammonium compounds in which the aliphatic radical can be a straight chain or branched, and wherein one of the aliphatic substituents contains from about 8 to 18 carbon atoms and one contains an anionic water solubilizing group, e.g., carboxy, sulfo, or sulfato. Examples of compounds falling within this definition are 3-(N,N-dimethyl-N-hexadecyl amino)-propane-1-sulfonate and 3-(N,N-dimethyl-N-hexadecyl amino)-2-hydroxypropane-1-sulfonate. In some circumstances, it may be desirable to use other types of defoamers, surfactants, and inhibitors.

Procedure

One procedure for producing a batch of the preferred additive for use in inks or a vehicle system is as follows:

1. Measure an amount of carboxylic acid, preferably 4,4'-carbonylbis (1,2-benzene-dicarboxylic acid), in the quantity for the batch size desired and pour into a container, such as a stainless steel pail.
2. Measure a sufficient quantity of water and dimethylaminoethyl methacrylate (MAME) for the selected batch size.
3. Place the stainless steel pail containing the BTA into a mixing tub on a drill press (mixer) and clamp the pail in place.
4. Fill the area around the pail in the mixing tub with ice and sufficient water to fill the mixing tub.
5. Install a mixing blade in the drill press.
6. Pour the water into the stainless steel pail containing the BTA.
7. Start mixing water and the BTA in the container by placing the mixing blades in the pail and rotating the mixing blades of the drill press at a medium speed. Reduce the temperature in the pail to 4° C. Wear goggles, mask, gloves, and coveralls. A white milky slurry will result. All the BTA may not be dissolved at this step, but it should be well mixed.
8. Cover the pail and do the next step in a darkroom. Light will destroy the product from this point on.
9. Slowly add MAME into the pail as the BTA and water continues to mix. This step generates great amounts of heat. The mixture should not be allowed to go above 10° C. or it can be destroyed.
10. Once MAME is added, keep the product (mixture) below 10° C. for at least two hours or less. Then remove the pail and allow the solution comprising the vehicle system additive to warm slowly to room temperature so it completes stabilization.
11. Package the vehicle system additive in an opaque container, such as a brown bottle. The vehicle system additive can be stored in a dark area and will be stable for many years without degradation. Do not store it in the sunlight, excessive heat or under ultraviolet emitting light or the additive may prematurely cure.

EXAMPLE 1

The above procedure was followed to prepare a batch of the additive. Specifically, 2.5 lbs. of water was added to 1 lb of 4,4'-carbonylbis-(1,2-benzene-dicarboxylic acid), and agitated to form a slurry. Thereafter, 1.75 lbs dimethylaminoethyl methacrylate (MAME) was trickled into the slurry in a darkroom. An exothermic reaction occurred. Trickling of MAME continued and the slurry reached a quasi-equilibrium state and became milky. As the slurry became clearer, MAME was added more quickly. The resultant product (vehicle system additive) had no free monomers and a pH of about 4.5. This additive should be buffered before use by adding a small amount of isopropyl alcohol, usually a few drops, sufficient to bring the pH to about 8.5. Monoethanolamine may be used instead.

EXAMPLE 2

A stock solution of the additive was made by adding 20 grams of orthobenzoylbenzoic acid to 150 grams of water. The mixture was stirred and chilled to 40° C. To this mixture 13.85 grams of dimethylaminoethyl-methacrylate (MAME) was added dropwise over a period of 90 minutes. During the addition of the MAME, the temperature was kept below 12° C. The MAME reacted with the orthobenzoylbenzoic acid to form the polyelectrolyte 2-benzophenone (carboxydimethylammonium-(ethylmethacrylate)) having the following structure:

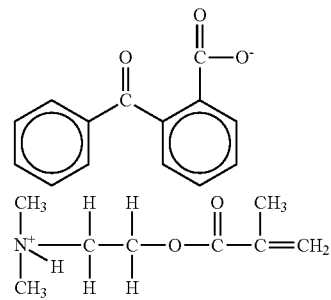

The additive water solution was then allowed to reach room temperature. This solution was stored in brown glass bottles for use at a later date.

EXAMPLE 3

A vehicle system was formulated by combining the oligomer additive stock solution of Example 2 with a fumaric resin (FILTREZ 5014) having an acid number over 170, an acrylic solution resin (CARBOSET GA-1931) and ink pigment dispersants. The ratio of fumaric resin to acrylic solution resin is preferably about 2:1 to about 4:1; and is more preferably about 3:1. A surfactant (e.g. SURFYNOL 465) was added to the vehicle system to reduce the surface tension from 72 dynes to 20 dynes. An inhibitor (VIRCO PET 40) and defoamer (FC-129) were also added to the vehicle system. The vehicle system comprised, by weight, 0.170 defoamer, 0.1% surfactants, and 0.2% inhibitors. The particle size of the black pigments of the pigment dispersants were 5-8 microns. The resultant vehicle system had essentially no free monomers or VOCs. The vehicle system was applied as an ink to a Gravure printing press operating at 2000 fpm at a depth less than 47 microns on the cylinders. The vehicle system transferred superbly onto paper at high speeds and did not undesirably stick, adhere or clog up the cylinders of the printing press. The printing press printed four color high quality pages of outstanding quality. The finished product had a gloss rating of about 85-90 degrees.

EXAMPLE 4

Coatings made with embodiments may be cured photochemically. The vehicle system of Example 3 was produced except that an acrylic emulsion resin (CARBOSET GA-1086) was used instead of fumaric resin and no additive was used. The vehicle system was applied as a coating to polypropylene and heated under ultraviolet (UV) bulbs. The vehicle system flocculated, and had essentially no VOCs or free monomers. The coating was cured, became hard, indicating cross-linking, and produced a superb product. Reasonable line speeds were achieved using 4 300-W UV lamps. The vehicle system was then prepared using the additive of Example 2. The formulation with the additive achieved the same line speed with a single 600-W UV curing lamp.

EXAMPLE 5

In one experiment, a coating formulation according to Example 3 was produced. The coating was applied to a wood veneer, heated in an oven at 150° F. (65° C.) for 5 minutes, and put into a UV (ultraviolet) tunnel. The coating was cured, became hard, and produced an excellent product.

EXAMPLE 6

A vehicle system was formulated as described in Example 5, but with paint pigment dispersants. The resultant vehicle system had essentially no free monomers or VOCs. The resultant vehicle system was applied by a spray gun as a paint on the metal body of an automobile and dried by ultraviolet (UV) heat lamps. The paint comprising the vehicle system had superb adhesion to the metal. The paint comprising the vehicle system also had an excellent attractive finish and formed a secondary film to prevent the color from beaching and fading.

EXAMPLE 7

An adhesive is formulated as described in Example 5, but with an adhesive polymer, i.e. Rohm and Haas Co. PS-68 polymer, useful for making pressure sensitive adhesives. Such a resin may act as a formulation for an adhesive. In one example, about 190.0 g adhesive is agitated and about 10.0 g of the additive of Example 1 is added slowly, making sure to control any exotherm. The resultant vehicle has essentially no free monomers or VOCs. The vehicle system may be applied as a pressure sensitive adhesive. The adhesive has excellent sticking and adhesive qualities, and because of the quicker coalescing, enables faster running of line speeds. One estimate is a three-fold increase, from about 200 feet per minute (FPM) to about 600 fpm in laminating paper.

The additive and vehicle system of this invention has produced unexpected surprisingly good results with inks, paints, coatings, and adhesives on numerous types of substrates including paper, paperboard, cardboard, clay coated board, metallic foils, films such as polyester and polyolefin films, wood, glass, and plastic.

EXAMPLE 8

A stock solution of the additive was made by adding 20.0 grams of orthobenzoylbenzoic acid to 150 grams of water. The mixture was stirred and chilled to 40° C. To this mixture 7.0 grams of dimethylethanolamine was added dropwise over a period of 90 minutes. During the addition of the dimethylethanolamine, the temperature was kept below 12° C. The resulting vehicle is very useful for flexographic, gravure, or offset lithographic inks.

EXAMPLE 9

A stock solution of the additive was made by adding 2.5 lb water to the vessel as described above, and stirring in 1.55 lb dimethylethanolamine. 0.80 lb formic acid was added slowly, to control the exotherm. Since none of these species is a photoinitiator, the procedure need not be carried out in the absence of light. The resulting pH was about 8.5. No additional buffering was needed before combining with an ink or coating for printing.

EXAMPLE 10

Another stock solution of the additive was made by adding 2.50 lb water to the vessel as described above for Example 9, and stirring in 1.83 lb dimethylethanolamine. 1.22 lb formic acid was added slowly, to control the exotherm. The resulting pH was about 8.5. No additional buffering is needed before combining with an ink or coating for printing.

The additive is useful for the preparation of inks, coatings, paints and adhesives, as in above Examples 3-7. The additive may also be added in situ to improve the performance (flocculation) of inks. In one trial, the stock solution additive of Example 10 was added to the ink system of an offset lithograph press, Speedmaster model, made by Heidelberg Press, between the second and third rolls of the ink system. The amount was about 2% by weight of the mass of ink in the system. As is well know, inks for lithographic printing are far more viscous than inks used in high volume processes, such as flexographic and gravure printing. As a result of the additive, throughput was improved by at least 10% because of improved flocculating and drying of the ink.

In general, we have found that our additive may be added directly to web heat set inks on the press, such as those inks made with hydrocarbon oils. We have also found that adding the additive directly to the ink system in offset lithography printing is also possible, especially with inks from vegetable oils, such as linseed oil or soybean oil. When the additive is about 50% solids, an amount of about 2 weight percent additive is sufficient to noticeably improve printing performance. More or less additive may also be used. Of course, the additive may also be mixed with an appropriate ink before the ink is charged to the press.

Additional Examples

Additional examples are presented in this section to show the great applicability of the additive. A vehicle for a water-based gravure ink may be formed by mixing about 60% FILTREZ 5014, about 25% CARBOSET GA-1931, and about 3.75% modifier and 11.25% water. The ink made with such a vehicle is very flowable and may be used at very high speeds on gravure presses.

A waterborne vehicle for flexographic inks may be made with a similar formulation, with about 60% CARBOSET GA-1086, about 25% GA-1931, and about 3.75% additive and 11.25% water. This vehicle readily forms inks that dry and cure quickly on flexographic printing equipment.

A vegetable based ink vehicle may be made by adding 5% additive or modifier to linseed or soybean oils. Alternatively, about 2% by weight of the modifier may be added to finished vegetable oil inks directly on the ink system of printing machinery. Presses on which trials have been successful include the Heidelberg Speedmaster model (Heidelberg, Germany), and one or more models from Komori Corp., Tokyo, Japan.

Water based coatings made be formulated by using a slightly greater amount of the additive. In one formulation, a coating is formed by mixing in about 40% high $T_g$ emulsion, about 30% low $T_g$ emulsion, about 10% high $T_g$ resin, and about 3% wax and 5% modifier, and 12% water.

Paints may also be formulated directly with the additive. A water-based paint may be formed by adding 5-10% of the additive directly to an acrylic emulsion, a resin solution, a resin emulsion, a latex resin solution, or a latex resin emulsion. An oil-based paint may be formulated by adding about 5-10% additive to a preferably refined and degummed vegetable oil, such as linseed or soybean oil. Paints made with the additive wet out pigment more effectively and have far less tendency to agglomerate. Thus, these coating may use lower loadings of pigment and are therefore more economical. These coating are also easy to apply and fast drying, with superior adhesion and greater hiding power. Coatings made with photoinitiator embodiments of the additive and applied to aluminum siding had virtually no chalking or fading after up to five years of outdoor exposure. Adhesion to difficult substrates, such as polymeric substrates, is greatly improved in coatings made with the additive.

Coatings

Two examples of coatings are presented, the coatings formulated with an additive made according to Example 1, above. In these examples, the additive was about 50% solids. In the formulations below, about 10% by weight additive was added to about 90% resin, by weight. Thus, in the first example, for an industrial maintenance glossy coating, 126.58 lbs of "Omnitech OT-204 Lot OH184" include 12.66 lbs of additive (50% solids) and 113.92 lbs Rohm & Hass Maincote HG-54D acrylic latex resin. In the second example, for a high quality interior flat, 59.67 lbs of "Omnitech OT-203 Lot OH-183" includes 5.97 lbs of additive (50% solids) and 53.70 lbs Rohm and Haas Rovace 9100 resin. The first coating is presented in Table I and the second coating is presented in Table 2.

It is clear from the test results, especially the VOC content, that the additive markedly improves the environmental acceptability of the coatings. In addition, these low VOC coatings were excellent coatings and applied easily.

TABLE I

Industrial Glossy Maintenance Coating

| Ingredient | Control, wt. lbs. | With additive, wt. lbs. |
|---|---|---|
| Downal DPM | 16.50 | — |
| Water | 35.00 | 35.00 |
| Tamol 165 | 8.50 | 8.50 |
| Aqueous ammonia (28%) | 1.00 | 1.00 |
| Triton CF-10 | 1.35 | 1.35 |
| TEGO 1488 | 1.35 | 1.35 |
| DuPont R-902 | 175.00 | 175.00 |
| Grind for 20 minutes | | |
| Maincote HG-54D | 595.00 | 464.77 |
| Omnitech OT-204 Lot OH-184 | — | 126.58 |
| Aqueous ammonia (28%) | 3.50 | 3.50 |
| Butyl cellosolve | 99.00 | — |
| TEGO 1488 | 2.35 | 2.35 |
| Sodium nitrite | 9.00 | 9.00 |
| Water | 21.72 | 21.72 |
| TOTAL | 969.27 | 850.12 |
| Lbs/gal | 9.69 | 9.77 |
| Weight percent solids | 44.76 | 44.12 |
| Volume percent solids | 34.64 | 34.65 |
| Test results: | | |
| VOC, grams/liter | 285 | 15 |

TABLE II

High Quality Interior Flat Coating

| Ingredient | Control, wt. lbs. | With additive, wt. lbs. |
|---|---|---|
| Water | 300.00 | 300.00 |
| Natrasol H4BR | 2.00 | 2.00 |
| Trysan 186-II | 1.80 | 1.80 |
| Tamol 731 | 6.00 | 6.00 |
| TEGO 1488 | 2.00 | 2.00 |
| KTPP[1] | 1.00 | 1.00 |
| Triton NP-9 (N-101) | 2.00 | 2.00 |
| Triton N-57 | 2.00 | 2.00 |
| Propylene Glycol | 45.00 | — |
| Huber 70C | 75.00 | 75.00 |
| DuPont R-902 | 200.00 | 200.00 |
| Camel White | 75.00 | 75.00 |
| Grind for 20 minutes | | |
| Rovace 9100 | 293.90 | 240.67 |
| Omnitech OT-203 Lot OH-183 | — | 59.67 |
| Downal DPNB | 13.00 | — |
| TEGO 1488 | 2.00 | 2.00 |
| Water | 64.44 | 112.83 |
| Acrysol RM-825 | 19.00 | 19.00 |
| Aqueous ammonia (28%) | 1.00 | 1.00 |
| TOTAL | 1105.14 | 1101.97 |
| Lbs/gal | 11.05 | 11.02 |
| Weight percent solids | 47.76 | 47.68 |
| Volume percent solids | 30.76 | 30.76 |
| Test results: | | |
| VOC, grams/liter | 196 | 17 |

[1] "Potassium tripolyphosphate" or pentapotassium triphosphate, $K_5P_3O_{10}$.

TABLE III

Industrial Glossy Maintenance Coating

| Ingredients, pounds | Control | w/ 0.6% additive | w/ 1.0% additive | w/ 1.3% additive |
|---|---|---|---|---|
| Downal DPM | 15.35 | 7.68 | 3.84 | — |
| Water | 35.00 | 35.00 | 35.00 | 35.00 |
| Tamol 165 | 7.91 | 7.91 | 7.91 | 7.91 |
| Aq. ammonia (28%) | 0.93 | — | — | — |
| Monoethanolamine | — | 0.93 | 0.93 | 0.93 |
| Triton CF-10 | 1.26 | 1.26 | 1.26 | 1.26 |
| TEGO 1488 | 1.86 | 1.86 | 1.86 | 1.86 |
| DuPont R-902 | 162.78 | 162.78 | 162.78 | 162.78 |
| Grind 20 minutes | | | | |
| Maincote HG-54D | 553.44 | 486.4 | 452.79 | 419.18 |
| HG-54D/10% additive | — | 62.03 | 93.05 | 124.07 |
| Ag. Ammonia (28%) | 3.26 | — | — | — |
| Monoethanolamine | — | 3.26 | 3.26 | 3.26 |
| TEGO 1488 | 2.79 | 2.79 | 2.79 | 2.79 |
| Water | 55.15 | 120.46 | 153.21 | 185.95 |
| Butyl cellosolve "EB" | 92.9 | 46.45 | 23.23 | — |
| Premix | | | | |
| Water/sodium nitrite | 4.00/8.00 | 4.00/8.00 | 4.00/8.00 | 4.00/8.00 |
| Acrysol RM-12W | 15.00 | 15.00 | 15.00 | 15.00 |
| TOTAL, lbs. | 959.63 | 965.81 | 968.91 | 971.99 |
| Lbs/gal | 9.60 | 9.66 | 9.69 | 9.72 |
| Weight percent solids | 42.35 | 42.18 | 42.10 | 42.02 |
| Volume percent solids | 32.56 | 32.57 | 32.57 | 32.57 |
| Test results: | | | | |
| VOC, grams/liter | 284 | 174 | 102 | 15 |

TABLE IV

High Quality Interior Flat Coating

| Ingredients, pounds | Control | w/ 0.55% additive | w/ 3.0% additive |
|---|---|---|---|
| Water | 300.00 | 300.00 | 300.00 |
| Natrosol H4BR | 2.00 | 2.00 | 2.00 |
| Troysan 186-II | 1.80 | 1.80 | 1.80 |
| Tamol 731 | 6.00 | 6.00 | 6.00 |
| TEGO 1488 | 2.00 | 2.00 | 2.00 |
| KTPP | 1.00 | 1.00 | 1.00 |
| Triton NP-9 (N-101) | 2.00 | 2.00 | 2.00 |
| Triton N-57 | 2.00 | 2.00 | 2.00 |
| Propylene glycol | 45.00 | — | — |
| Huber 70C | 75.00 | 75.00 | 75.00 |
| DuPont R-902 | 200.00 | 200.00 | 200.00 |
| Camel White | 75.00 | 75.00 | 75.00 |
| Grind for 20 minutes | | | |
| Rovace 9100 | 293.90 | 240.67 | — |
| Additive, OH-203 | — | 59.67 | 332.2 |
| Downal DPNB | 13.00 | — | — |
| TEGO 1488 | 2.00 | 2.00 | 2.00 |
| Water | 64.44 | 112.83 | 38.34 |
| Acrysol RM-825 | 19.00 | 19.00 | 19.00 |
| Aq. ammonia (28%) | 1.00 | 1.00 | 1.00 |
| TOTAL, lbs. | 1105.14 | 1101.97 | 1092.66 |
| Lbs/gal | 11.05 | 11.02 | 10.93 |
| Weight percent solids | 47.76 | 47.68 | 47.19 |
| Volume percent solids | 30.76 | 30.76 | 30.76 |
| Test results: | | | |
| VOC, grams/liter | 196 | 17 | 17 |

TABLE V

High Quality Exterior Satin Gloss Coating

| Ingredients, pounds | Control | w/ 0.85% additive | w/ 3.9% additive |
|---|---|---|---|
| Water | 43.10 | 43.10 | 83.30 |
| Propylene glycol | 40.00 | — | — |
| Troysan 186-II | 1.80 | 1.80 | 1.80 |
| Tamol 731 | 10.00 | 10.00 | 10.00 |
| TEGO 1488 | 2.00 | 2.00 | 2.00 |
| Triton CF-10 | 2.00 | 2.00 | 2.00 |
| Dimethylethanolamine | 2.00 | 2.00 | 2.00 |
| Mix for 10 minutes | | | |
| Huber 70C | 60.00 | 60.00 | 60.00 |
| DuPont R-902 | 250.00 | 250.00 | 250.00 |
| Grind for 20 minutes | | | |
| Rhoplex AC-264 | 465.00 | 364.88 | — |
| 10% additive, OH-205 | — | 92.60 | 429.67 |
| TEGO 1488 | 6.00 | 6.00 | 6.00 |
| Propylene glycol | 35.00 | — | — |
| Texanol[2] | 14.00 | — | — |
| Water | 157.06 | 251.29 | 238.35 |
| Natrosol H4BR | 3.98 | 3.98 | 3.98 |
| TOTAL, lbs. | 1091.94 | 1089.65 | 1089.10 |
| Lbs/gal | 10.92 | 10.90 | 10.89 |
| Weight percent solids | 55.26 | 55.38 | 55.43 |
| Volume percent solids | 41.83 | 41.84 | 41.84 |
| Test results: | | | |
| VOC, grams/liter | 208 | 6 | 6 |

[2] 2,2,4-Trimethyl-1,3-pentanediol monoisobutyrate, $C_{12}H_{24}O_3$, CAS #25265-77-4.

Additional examples were also prepared to test the limits of the additive, and are shown below in three additional tables. Table III shows how additional amounts of the additive progressively lowers VOC. In Table III, the additive included 70% acrylic emulsion, HG-54D, 10% water, 10% additive according to Example 1 above, and 2% S160 (mildewcide, Ferro Corp., Walton Hills, Ohio).

Table IV, with a different acrylic emulsion, Rovace 9100 from Rohm & Haas, shows that as little as about 0.5-0.7% of the additive is effective in lowering VOC with no corresponding loss of performance.

Table V, with a different acrylic emulsion, Rhoplex AC-264 from Rohm & Haas, provides another example with excellent performance. The additive in Table V was 90% Rhoplex AC264, 10% additive according to Example 1 above. Tables I-V also show that coatings may be made from a vehicle using only two components, the additive and the base resin, in these cases an acrylic emulsion.

Advantages of the Additive

Among the many advantages of the vehicle system and additive of this invention are rapid high speed transfer between the press and the substrate to which the ink is applied. Other advantages include superb adhesion to the substrate, outstanding product performance, and excellent protective coatings. With proper pigmentation, the coatings may prevent colors from fading, and are useful on many different substrates. Because VOCs are virtually not used in the formulation, vehicles and inks, coatings, paints and adhesives will more readily comply with environmental laws on airborne emissions, since there are virtually no VOCs in the formulations. and thus will be beneficial to the environment.

Vehicles and inks made with the additive have superior quality and free monomers in the additive and the vehicle are decreased. Coatings and adhesives made with the additive have excellent strength. Inks flocculate quickly, dry quickly, and do not clog printing presses. The additive and vehicles made from the additive are easy to use. Inks and coatings made with the additive or vehicles using the additive are attractive, economical reliable, safe, efficient and effective.

Although embodiments of the invention have been shown and described, it is to be understood that various modifications and substitutions, as well as rearrangements of parts, components, and process steps, can be made by those skilled in the art without departing from the novel spirit and scope of this invention. For instance, it is easier to control the reaction between the acid or anhydride with the acrylate, methacrylate, or amino compound of the additive, if a slurry or solution with the acid or anhydride is made first. This allows dissipation of the heat of solution of the acid, and allows for better mixing of high molecular weight carboxylic acids or anhydrides that are not very soluble, to form a slurry. Then, when the other compound is added, preferably dripwise or very slowly, the exotherm is easier to control. However, the order of addition could be reversed with appropriate care to insure that the acid or anhydride, which may be in solid form, disperses well and does not cause an explosive exotherm. Both methods of forming the additive are meant to be included as embodiments.

While it is typical to form a vehicle for inks or paints in a mixing vessel, and then to incorporate the vehicle into a formulation for an ink, a paint, a coating, and so forth, it has been shown that the additive may be prepared separately and added to the inking system of a printing press. This method of addition to form an ink, paint, coating, and so forth, are embodiments, as is the ink, paint, coating, and so forth that are formed in this manner.

It will also be understood that inks, paints, coatings and adhesives may include many other components not discussed herein, and well-known to those skilled in the art. For example, vegetable oil compositions, such as those using linseed oil, may require catalysts or activators to oxidize or cure. These may include one or more of cobalt acetate, manganese acetate, calcium stearate, or other activators, such as those using rare-earth elements. Embodiments of the invention will include such well-known components otherwise necessary for the proper functioning and performance of compositions made with the vehicle or additive described above.

It is therefore intended that the foregoing detailed description be regarded as illustrative rather than limiting, and that it be understood that it is the following claims, including all equivalents, that are intended to define the spirit and scope of this invention.

What is claimed is:

1. A vehicle system, comprising by weight relative to the vehicle system:
   (a) about 4-45% of a first component, the first component comprising at least one material selected from the group consisting of an acrylic resin solution, a latex dispersion, a urethane solution, a microcrystalline wax solution, and a vegetable oil;
   (b) about 50-90% of a second component, the second component comprising at least one material selected from the group consisting of a fumaric resin solution and an acrylic resin emulsion; and
   (c) about 0.5-10% of an aqueous solution of an additive comprising the reaction product of
      (i) a first reagent comprising a carboxylic acid; and
      (ii) a second reagent comprising at least one material selected from the group consisting of a dialkylaminoalkyl acrylate monomer, and a dialkylaminoalkyl methacrylate monomer.

2. The vehicle system of claim 1, wherein the additive is capable of being activated by heat to cause phase separation of the vehicle system.

3. The vehicle system of claim 1, wherein the additive is capable of being cured photochemically.

4. The vehicle system of claim 1, wherein the first component comprises acrylic resin solution, the second component comprises a fumaric resin solution, and the weight ratio of fumaric resin to acrylic resin is from about 2:1 to about 4:1.

5. The vehicle system of claim 1, wherein the first component comprises about 2-50% by weight of acrylic resin, water up to about 75% by weight, and about 0-20% by weight of a diluting agent.

6. The vehicle system of claim 1, wherein the second component comprises about 2-50% by weight of fumaric resin, water up to about 75% by weight, and about 0-30% by weight of a diluting agent.

7. The vehicle system of claim 1, wherein the first component comprises a urethane dispersion of about 25 percent to about 50 percent by weight solids in an aqueous solution.

8. The vehicle system of claim 1, wherein the first component is selected from the group consisting of corn oil, cottonseed oil, olive oil, palm oil, palm kernel oil, peanut oil, linseed oil, soybean oil, tall oil, and tung oil.

9. The vehicle system of claim 1, wherein the second component comprises about 50-100% by weight acrylic emulsion resin and water up to about 30% by weight.

10. A paint, ink, or coating comprising the vehicle system of claim 1.

11. A paint, ink, or coating comprising the vehicle system of claim 1, further comprising at least one of
   i) a surfactant in an amount of about 0.05 to 0.5 weight percent;
   ii) a defoamer in an amount of about 0.05 to 0.5 weight percent; and
   iii) an inhibitor in an amount of about 0.05 to 2.0 weight percent.

12. A vehicle system, comprising by weight relative to the vehicle system:
   (a) about 4-45% of a first component comprising at least one material selected from the group consisting of an acrylic resin solution, a latex dispersion, a paraffin solution, a paraffin emulsion, a urethane resin solution and a vegetable oil;
   (b) about 50-90% of a second component comprising at least one material selected from the group consisting of a fumaric resin solution and an acrylic resin emulsion; and
   (c) about 0.5-10% additive in aqueous solution comprising the reaction product of
      (i) a first reagent comprising carboxylic acid and containing a benzene ring; and
      (ii) a second reagent comprising at least one material selected from the group consisting of an alkylaminoalkyl acrylate monomer and an alkylaminoalkyl methacrylate monomer.

13. An ink, coating, or adhesive made with the vehicle according to claim 12.

14. A vehicle system, comprising by weight relative to the vehicle system:
   (a) about 80-99% of a first component comprising at least one material selected from the group consisting of an acrylic resin solution, a urethane resin solution, a latex dispersion, a wax dispersion or emulsion, a fumaric resin solution, and a vegetable oil; and (b) about 1-20 additive comprising in aqueous solution the reaction product of
  (i) a first reagent comprising a carboxylic acid; and
  (ii) a second reagent comprising at least one material selected from the group consisting of a dialkylaminoalkyl acrylate monomer, and a dialkylaminoalkyl methacrylate monomer.

15. The vehicle system of claim 14, wherein the second reagent is selected from the group consisting of N,N-dimethylaminoethyl acrylate, N,N-dimethylaminoethyl methacrylate; N,N-diethylaminoethyl acrylate, N,N-diethylaminopropyl acrylate, N,N-dimethylaminoethyl methacrylate, N,N-diethylaminoethyl methacrylate, N,N-diethylaminopropyl methacrylate, N,N- diethylaminopropyl acrylate; N,N-diethylaminobutyl methacrylate; and N,N-diethylaminobutyl acrylate.

16. The vehicle system of claim 14, wherein the additive comprises the reaction product of 3,3',4,4'-benzophenonetetracarboxylic acid and N,N-dimethylaminoethyl-methacrylate.

17. The vehicle system of claim 14, wherein the first component comprises about 50-100% by weight acrylic emulsion resin and water up to about 30% by weight.

18. An ink, coating, or adhesive made with the vehicle according to claim 14.

19. The paint, ink, or coating of claim 14, further comprising at least one of an inhibitor in an amount of about 0.05 to 2.0 weight percent, a surfactant in an amount of about 0.05 to 0.5 weight percent, and a defoamer in an amount of about 0.05 to 0.5 weight percent.

20. An ink comprising the vehicle system of claim 1, wherein the first component is an acrylic resin solution;
  wherein the second component is a fumaric resin solution;
  wherein the first reagent is a carboxylic acid; and
  wherein the second reagent is a dialkylaminoalkyl methacrylate.

* * * * *